United States Patent
Dacosta et al.

(10) Patent No.: US 9,980,760 B2
(45) Date of Patent: May 29, 2018

(54) STEP OFF BONE PLATES, SYSTEMS, AND METHODS OF USE

(71) Applicant: Paragon 28, Inc., Englewood, CO (US)

(72) Inventors: Albert Dacosta, Lone Tree, CO (US); Joshua Clendenin, Denver, CO (US)

(73) Assignee: PARAGON 28, INC., Englewood, CO (US)

( * ) Notice: Subject to any disclaimer, the term of this patent is extended or adjusted under 35 U.S.C. 154(b) by 688 days.

(21) Appl. No.: 14/547,616

(22) Filed: Nov. 19, 2014

(65) Prior Publication Data

US 2016/0135858 A1    May 19, 2016

(51) Int. Cl.
  *A61B 17/80* (2006.01)
  *A61B 17/17* (2006.01)
  *A61B 17/56* (2006.01)
  *A61B 17/15* (2006.01)

(52) U.S. Cl.
  CPC .......... *A61B 17/80* (2013.01); *A61B 17/1728* (2013.01); *A61B 17/808* (2013.01); *A61B 17/8061* (2013.01); *A61B 17/151* (2013.01); *A61B 2017/564* (2013.01)

(58) Field of Classification Search
  CPC ................. A61B 17/8061; A61B 17/1682
  See application file for complete search history.

(56) References Cited

U.S. PATENT DOCUMENTS

| | | | |
|---|---|---|---|
| 6,342,057 B1 | 1/2002 | Brace et al. | |
| 6,692,496 B1 | 2/2004 | Wardlaw | |
| 7,011,665 B2 | 3/2006 | Null et al. | |
| 7,819,877 B2 | 10/2010 | Guzman et al. | |
| 8,080,010 B2 * | 12/2011 | Schulz | A61B 17/15 606/280 |
| 8,231,627 B2 | 7/2012 | Huebner et al. | |
| 8,764,807 B2 | 7/2014 | Michel et al. | |
| 9,283,008 B2 * | 3/2016 | Gonzalez-Hernandez | A61B 17/8085 |
| 2005/0033301 A1 | 2/2005 | Lombardo et al. | |
| 2006/0189996 A1 | 8/2006 | Orbay et al. | |
| 2007/0173843 A1 * | 7/2007 | Matityahu | A61B 17/80 606/916 |
| 2007/0225714 A1 | 9/2007 | Gradl | |

(Continued)

FOREIGN PATENT DOCUMENTS

| | | |
|---|---|---|
| CN | 201223440 Y | 4/2009 |
| CN | 201365972 Y | 12/2009 |

(Continued)

OTHER PUBLICATIONS

Extended European Search Report issued in European Application EP 15195121.7 dated Oct. 18, 2016.

*Primary Examiner* — Andrew Yang
(74) *Attorney, Agent, or Firm* — Heslin Rothenberg Farley & Mesiti P.C.

(57) ABSTRACT

The present invention discloses a step off bone plate, bone plate insertion system, and method of use. The step off bone plate includes a body with a first end and a second end, the body includes a first portion with a first curvature, a second portion with a second curvature, and a connecting portion coupled to the first portion at a first end and coupled to the second portion at a second end. The bone plate insertion system includes a step off bone plate and an alignment guide apparatus. A method of using the step off bone plate is also disclosed.

19 Claims, 22 Drawing Sheets

(56) References Cited

U.S. PATENT DOCUMENTS

| | | |
|---|---|---|
| 2007/0239168 A1 | 10/2007 | Keunzi et al. |
| 2008/0021452 A1 | 1/2008 | Ducharme et al. |
| 2009/0036931 A1 | 2/2009 | Pech et al. |
| 2010/0087824 A1 | 4/2010 | Collazo |
| 2011/0218576 A1 | 9/2011 | Galm et al. |
| 2011/0264149 A1 | 10/2011 | Pappalardo et al. |
| 2012/0078252 A1 | 3/2012 | Huebner et al. |
| 2012/0303038 A1 | 11/2012 | Durante et al. |
| 2014/0148859 A1 | 5/2014 | Taylor et al. |
| 2014/0180348 A1 | 6/2014 | Thoren et al. |
| 2014/0309703 A1 | 10/2014 | Ducharme et al. |
| 2015/0359580 A1 | 12/2015 | Dacosta et al. |

FOREIGN PATENT DOCUMENTS

| | | |
|---|---|---|
| CN | 202218914 U | 5/2012 |
| CN | 203417254 U | 2/2014 |
| DE | 102007047576 A1 | 4/2009 |
| EP | 0617927 A1 | 10/1994 |
| EP | 1273271 | 1/2003 |
| EP | 1897509 A1 | 3/2008 |
| EP | 2762098 A2 | 8/2014 |
| FR | 2706763 A1 | 12/1994 |
| JP | 04250156 | 9/1992 |
| WO | 1994015556 | 7/1994 |
| WO | 2009105201 A1 | 8/2009 |
| WO | 2010059497 A1 | 5/2010 |
| WO | 2014105750 A1 | 7/2014 |
| WO | 2014140886 A2 | 9/2014 |
| WO | 2015094409 | 6/2015 |

\* cited by examiner

STEP OFF BONE PLATES, SYSTEMS, AND METHODS OF USE

FIELD OF THE INVENTION

The present invention relates generally to the field of orthopedics related to orthopedic bone plates, specifically, step off bone plates, bone plate insertion systems, and methods for using the bone plates.

BACKGROUND OF THE INVENTION

Currently, the lapidus procedure is performed at the base of the first metatarsal and involves the cuneiform. Typically, surgeons perform sagittal saw cuts to provide the proper realignment of the joint. The cutting of the joint shortens the first metatarsal and could off load the sesamoids which may alter normal pressures on the foot. In order to correct for this shortening, surgeons will not only correct the position in the transverse plane (hallux valgus), but will also plantar translate or angulate the metatarsal to reload the sesamoids. In order to achieve this, surgeons may utilize an off-set style plate that is positioned dorsal medial on the joint thus translating the cut bone down and over. However, a dorsal medial positioned plate is not ideal due to the forces imparted on the plate post-operatively.

Accordingly, the present invention contemplates a newly configured and improved bone plate and methods which overcome the above-referenced problems and others.

SUMMARY OF THE INVENTION

The present invention is directed toward step off bone plates, bone plate insertion systems, and methods of using the devices.

In one aspect, provided herein is a step off bone plate. The step off bone plate may include, for example, a body with a first end and a second end. The body may include a first portion with a first curvature, a second portion with a second curvature, and a connecting portion coupled to the first portion at a first end and coupled to the second portion at a second end.

In another aspect, provided herein is a bone plate insertion system. The bone plate insertion system may include, for example, a bone plate with a first and second end and an alignment guide apparatus. The bone plate may include, for example, a first portion with a first curvature, a second portion with a second curvature, and a connecting portion. The connecting portion connects the first portion to the second portion.

In yet another aspect, provided herein is a method for using the step off bone plate. The method includes, for example, preparing and aligning a patient's bones. The method may also include selecting a step off bone plate and attaching an insertion guide to the step off bone plate. The method may further include aligning the step off bone plate over the bones and securing the bone plate to the bones with temporary fixation members. In addition, the method may include inserting a guide wire through the insertion guide and across the bones and removing the insertion guide from the step off bone plate. The method may further include inserting a screw over the guide wire and across the bones. The method may also include inserting bone screws to secure the plate to the patient's bones. Further, the method may include closing the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Figure 1:
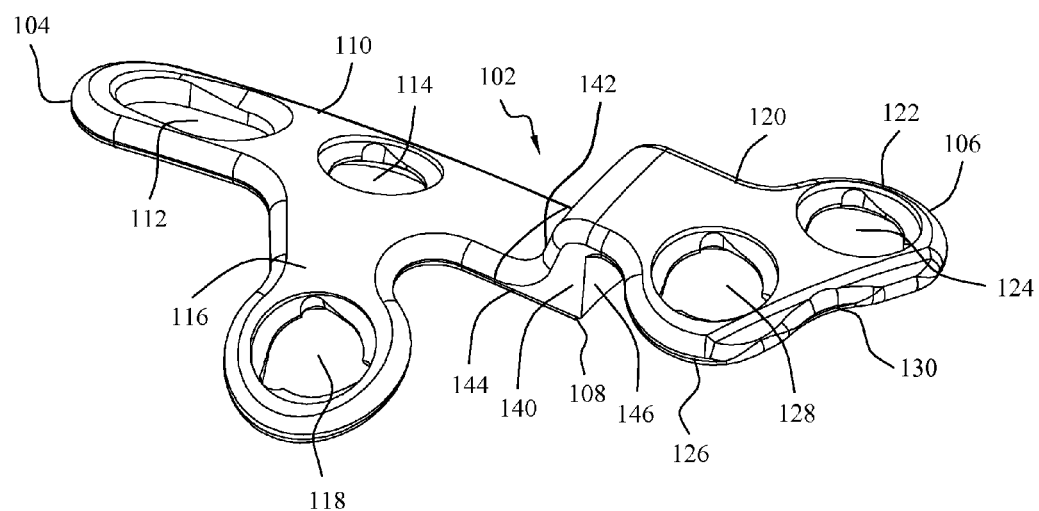
FIG. 1 is a top perspective view of a step off bone plate, in accordance with an aspect of the present invention.
Figure 2:
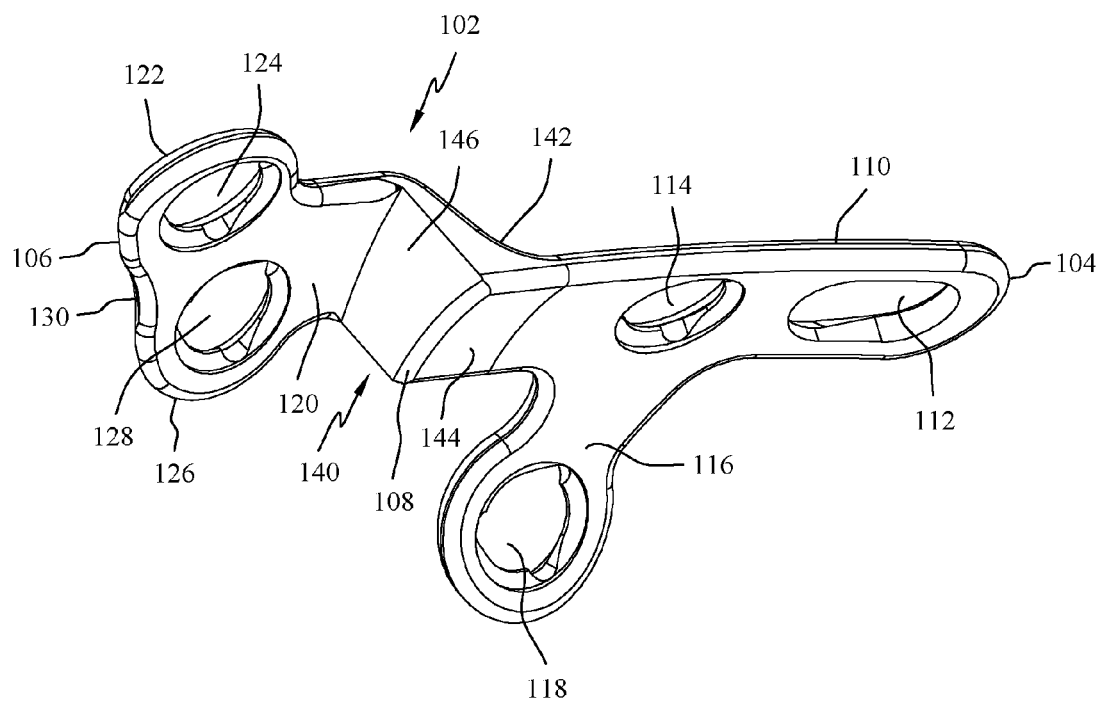
FIG. 2 is a bottom perspective view of the step off bone plate of FIG. 1, in accordance with an aspect of the present invention.

Generally stated, disclosed herein is an embodiment of a step off bone plate. The terms "step off bone plate," "bone plate," and "plate" may be used interchangeably herein as they essentially refer to the same device. Further, a method for using the step off bone plate is discussed.

In this detailed description and the following claims, the words proximal, distal, anterior, posterior, medial, lateral, superior, inferior, dorsal and plantar are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Referring to the drawings, wherein like reference numerals are used to indicate like or analogous components throughout the several views, and with particular reference to FIGS. 1-8, a bone plate 100, for example, a step off bone plate, is shown. The bone plate 100 is designed for medial wall positioning to provide a bone plate 100 with a dual curvature along the long axis of the plate 100 to match the correction of a more dorsally located plate. The dual curvatures of the plate 100 allow for the plate 100 to be positioned medially thereby providing a more stable construct and a plate that resists bending.

The step off bone plate 100, as shown in FIGS. 1-8, includes a body 102 with a first end 104, a second end 106, and a transition point 108 positioned between the first end 104 and the second end 106. The body 102 may include a first portion 110, a second portion 120, and a connecting portion 140 coupling the first portion 110 to the second portion 120. The first portion 110 may extend from the first end 104 to the transition point 108. The second portion 120 may extend from the transition point 108 to the second end 106. The connecting portion 140 may be positioned between the first portion 110 and second portion 120 at the transition point 108.

Figure 3:
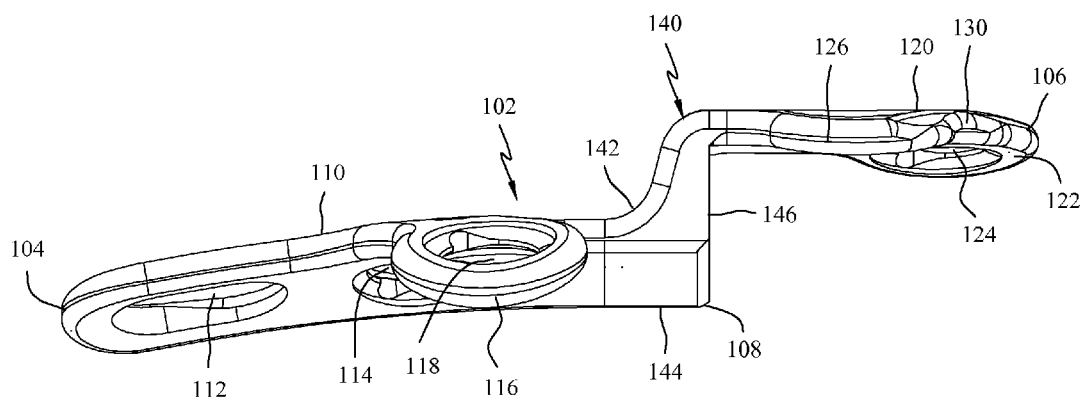
FIG. 3 a first side view of the step off bone plate of FIG. 1, in accordance with an aspect of the present invention.
Figure 4:
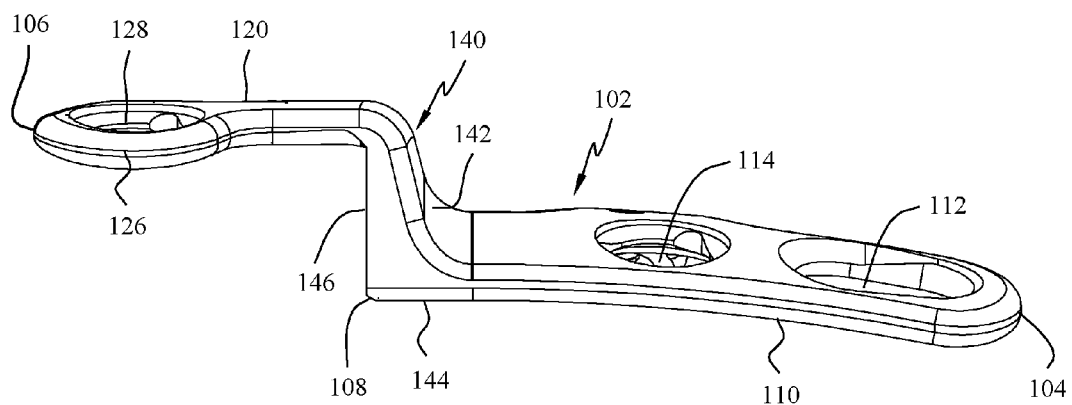
FIG. 4 is a second side view of the step off bone plate of FIG. 1, in accordance with an aspect of the present invention.
Figure 5:
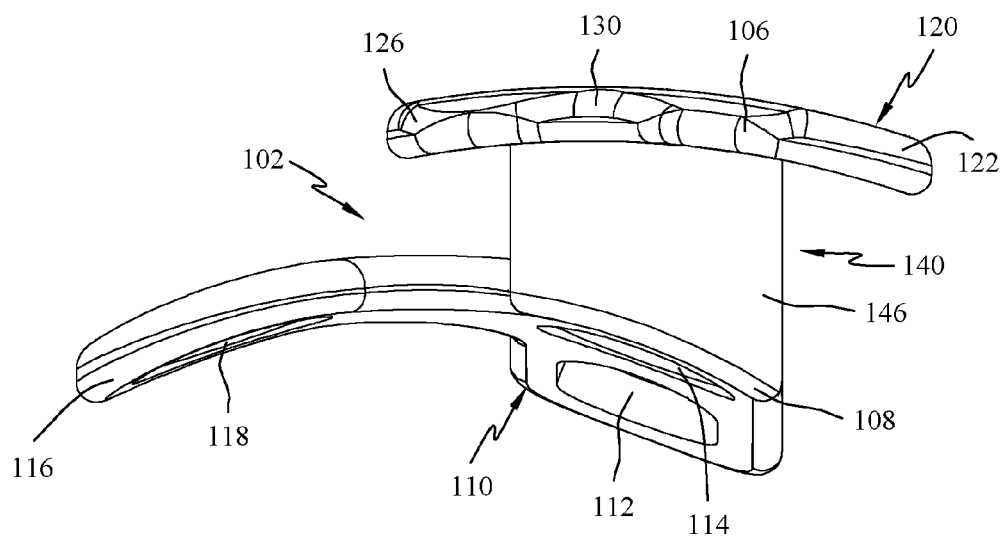
FIG. 5 is a front view of the step off bone plate of FIG. 1, in accordance with an aspect of the present invention.

As shown in FIGS. 1-8, the first portion 110 may have at least one slot 112 near the first end 104 of the body 102 and at least one first opening 114 positioned between the at least one slot 112 and the transition point 108. As depicted, the at least one first opening 114 may be positioned adjacent to the at least one slot 112. The slot 112 and first opening 114 may be, for example, aligned along the center of the body 102. The opening 114 may be, for example, a screw hole for receiving a threaded fastener or screw (not shown). The first portion 110 may also include an extension member or arm 116, as shown in FIGS. 1-3 and 5-8. The extension member 116 may extend out from a side of the body 102 of the first portion 110 and may include at least one second opening 118. The extension member 116 may extend out from the body between the first end 104 and the transition point 108 and may be angled with respect to the longitudinal axis of the body 102. For example, the extension member 116 may extend out from the body near the first opening 114. The extension member 116 may be angled toward the second end 106 of the body 102. The extension member 116 may also be curved as it extends away from the body 102 as seen in FIG. 5. The curvature of the extension member 116 may, for example, match the curvature of the bone engaging the first portion 110. The extension member 116 may be configured to reinforce the plantar aspect of the foot to reduce or restrict gapping after surgery by providing plantar support from a medial positioned plate 100. The extension member 116 may also be positioned in the direction that matches the normal transition of stress during the gait cycle to provide the greatest strength during peak loads. The first portion 110 of the plate 100 may include a dual curvature with, for example, a first curvature perpendicular to the long axis of the plate 100 and a second curvature along the long axis of the plate 100. The first curvature may have a radius of, for example, approximately 8 mm to 60 mm, and the second curvature may have a radius of, for example, approximately 50 mm to 300 mm.

The second portion 120, as shown in FIGS. 1-2 and 7-8, may include a first lobe 122 and a second lobe 126 extending out from the body 102. The first lobe 122 may be offset from the second lobe 126 forming an angled surface at the second end 106 of the body 102 as seen in FIG. 5. The first lobe 122 may include a third opening 124 and the second lobe 124 may include a fourth opening 128. Alternative numbers of lobes 122, 126 are also contemplated to provide for additional fastening locations for securing the plate 100 to the patient's bones. The openings 124, 128 may be, for example, screw holes for receiving threaded fasteners or screws (not shown). The second portion 120 may also include a ramped portion 130 positioned at the second end 106 along the angled surface. The ramped portion 130 is gradually angled from the bottom surface to the top surface of the body 102 and provides a surface that allows a tendon, for example, the anterior tibialis tendon, to glide over the plate 100. By allowing the tendon to glide over the plate soft-tissue irritation is eliminated. Existing plate designs cause the tendon to pop or jump over the plate resulting in patient discomfort. The ramped portion 130 may decrease the thickness of the plate at the second end 106, while still maintaining adequate thickness to prevent screw prominence.

Referring now to FIGS. 1-4, the connecting portion 140 is positioned relatively perpendicular to and couples the first portion 110 and the second portion 120. The connecting portion 140 provides a change in elevation or "step up" from the first portion 110 to the second portion 120. The connecting portion 140 may provide a step up of, for example, approximately 1 mm to 10 mm. The connecting portion 140 may include a sloped surface 142 on the top of the body 102. In addition, the connecting portion 140 may include a first transition portion 144 extending from the first portion 110 to the transition point 108 and a second transition portion 146 extending perpendicular to the first transition portion 144 from the transition point 108 to the second portion 120. The first transition portion 144 and second transition portion 146 may be relatively planar.

Figure 6:
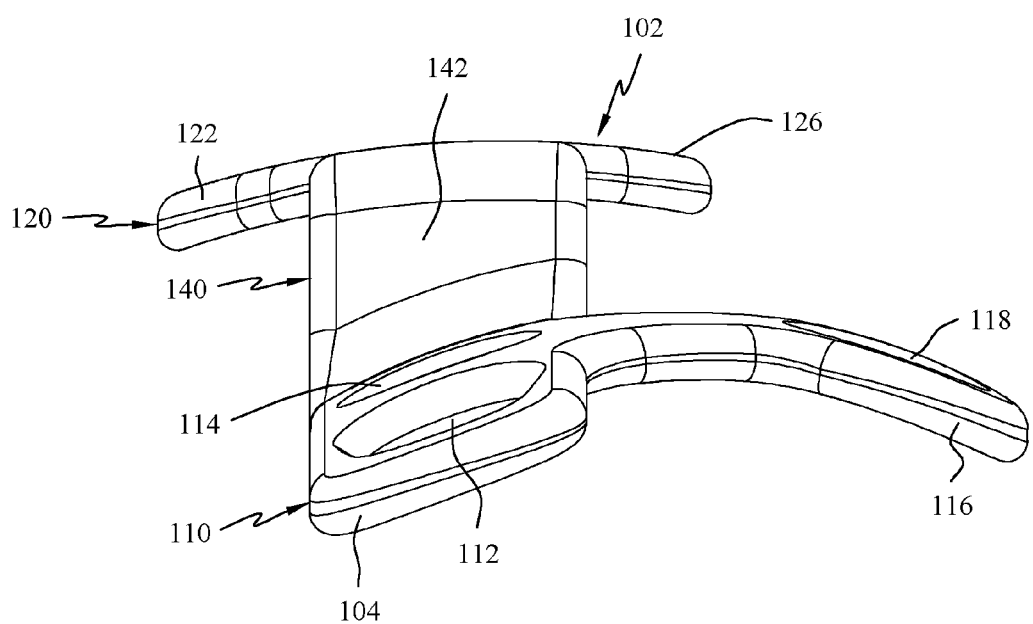
FIG. 6 is a back view of the step off bone plate of FIG. 1, in accordance with an aspect of the present invention.
Figure 7:
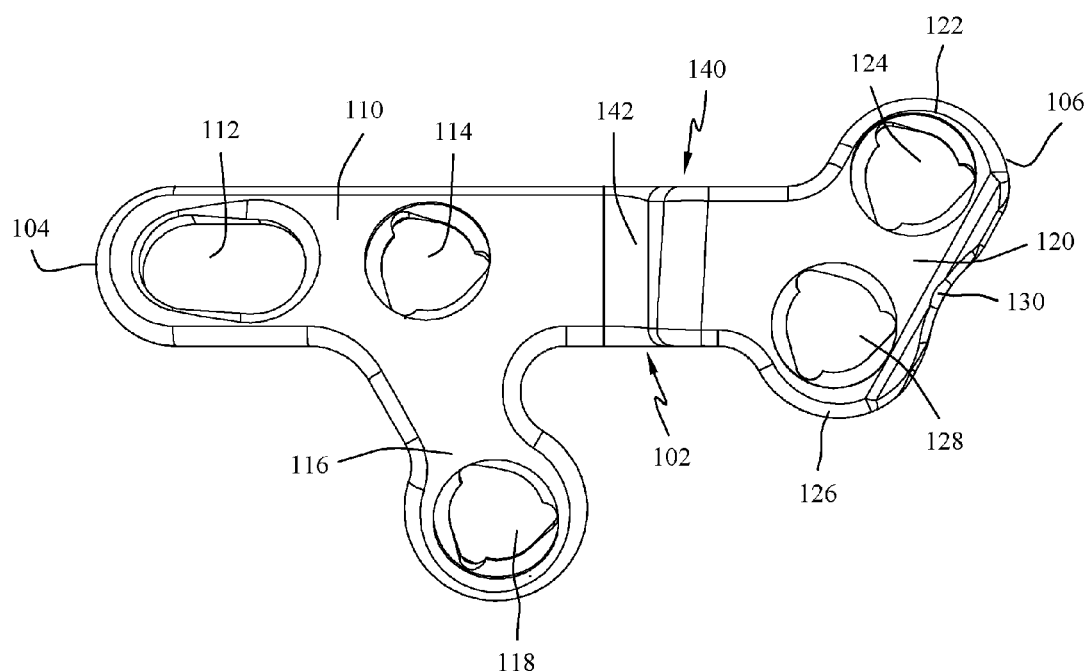
FIG. 7 is a top view of the step off bone plate of FIG. 1, in accordance with an aspect of the present invention.
Figure 8:
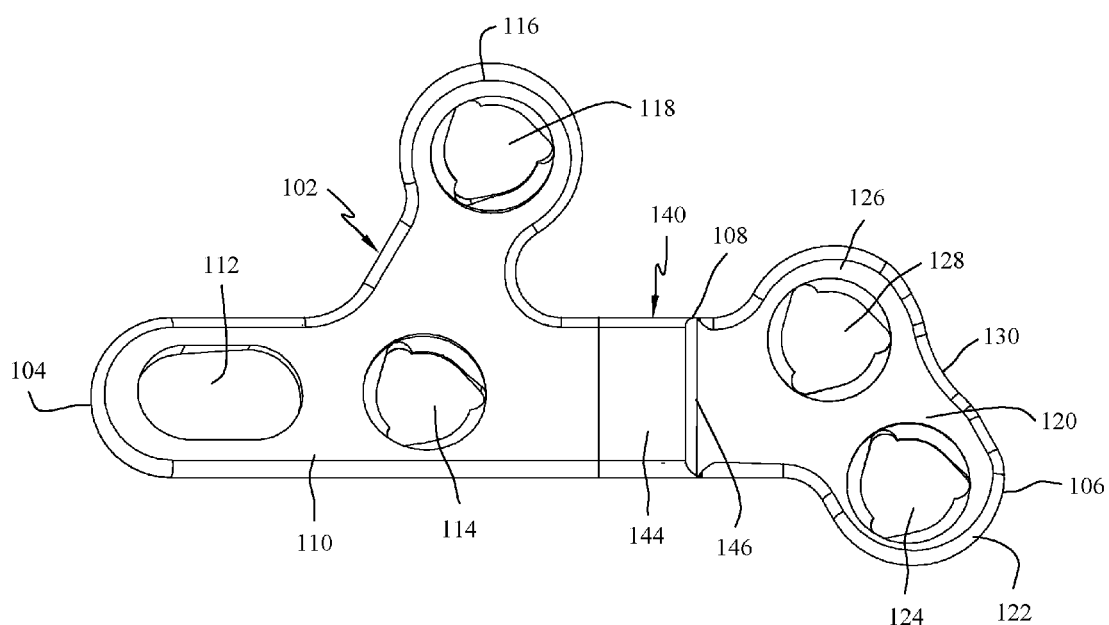
FIG. 8 is a bottom view of the step off bone plate of FIG. 1, in accordance with an aspect of the present invention.
Figure 9:
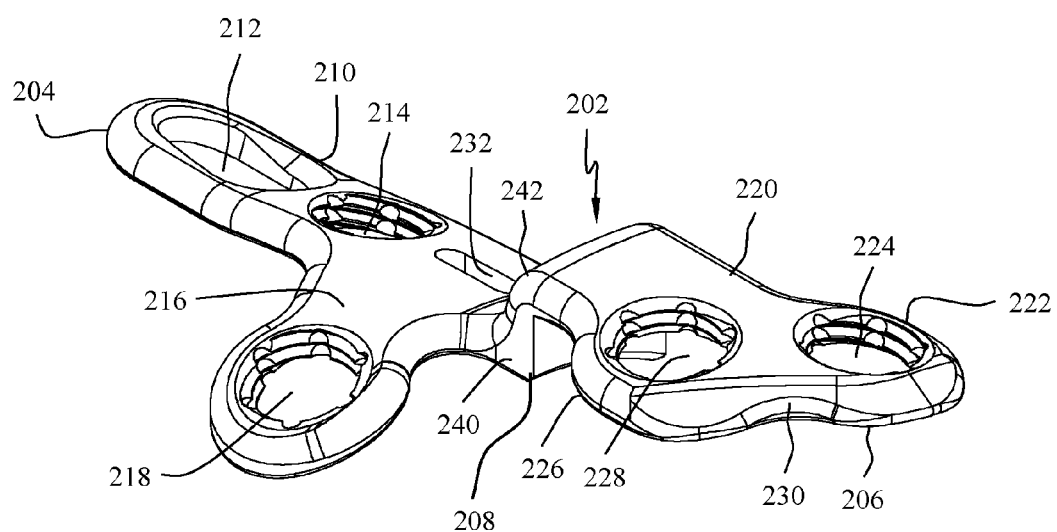
FIG. 9 is a top perspective view of another step off bone plate, in accordance with an aspect of the present invention.
Figure 10:
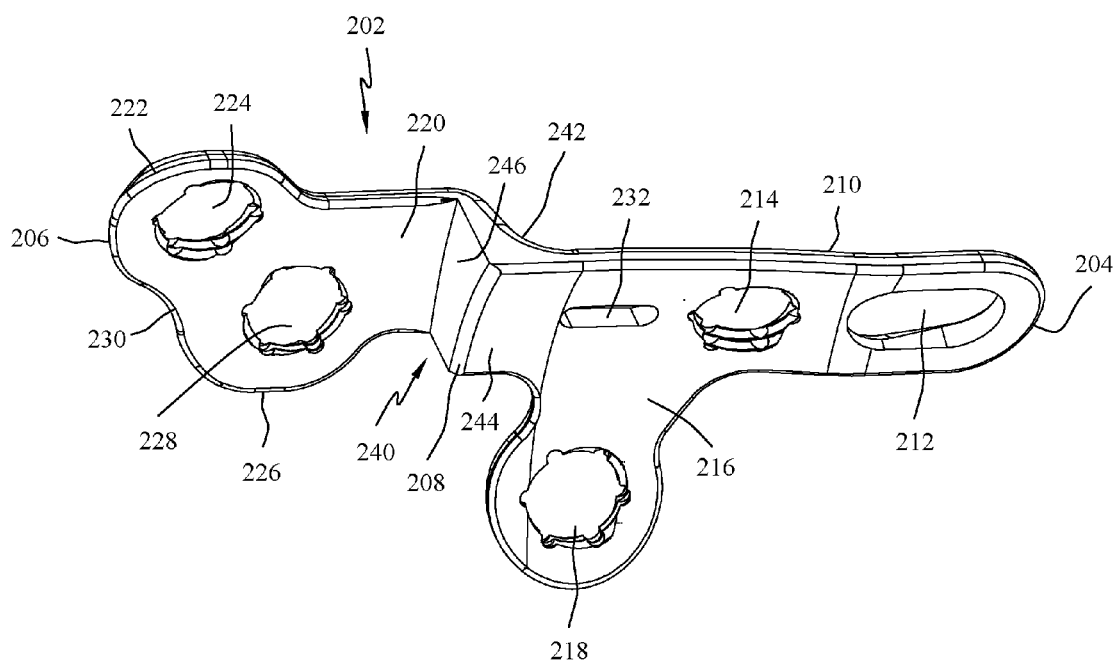
FIG. 10 is a bottom perspective view of the step off bone plate of FIG. 9, in accordance with an aspect of the present invention.

As shown in FIGS. 3-6, the plate 100 may include multiple curved surfaces. The plate 100 may include dual curvatures with respect to the longitudinal axis of the plate 100, as shown in FIGS. 5-6. The first portion 110 may have a first curvature in a medial-lateral direction with respect to the longitudinal axis of the plate 100. The first curvature may have a range of, for example, approximately 8 mm to 60 mm. The second portion 120 may have a second curvature in the medial-lateral direction along with respect to the longitudinal axis of the plate 100 along the bottom surface. The second curvature may have a range from, for example, approximately 10 mm to 60 mm. The first curvature and second curvature may be different in plate 100 to allow for the plate 100 to be used on the medial aspect of a patient's foot. As shown in FIGS. 3-4, the body 102 of the plate 100 may have a third curvature in line with the longitudinal axis and the third curvature may have a range of, for example, approximately 50 mm to 300 mm.

Referring now to FIGS. 9-16, another step off bone plate 200 is shown. The bone plate 200 may include a body 202 with a first end 204, a second end 206, and a transition point 208 positioned between the first end 204 and the second end 206. The body 202 may include a first portion 210, a second portion 220, and a connecting portion 240 attaching the first portion 210 to the second portion 220. The first portion 210 may extend from the first end 204 to the transition point 208. The second portion 220 may extend from the transition point 208 to the second end 206. The connecting portion 240 may be positioned between the first portion 210 and second portion 220 at the transition point 208.

Figure 11:
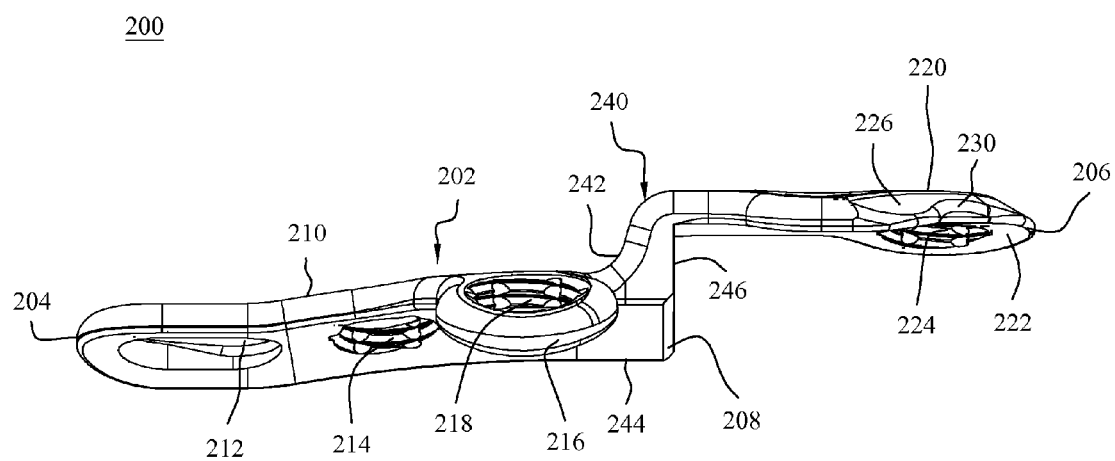
FIG. 11 a first side view of the step off bone plate of FIG. 9, in accordance with an aspect of the present invention.
Figure 12:
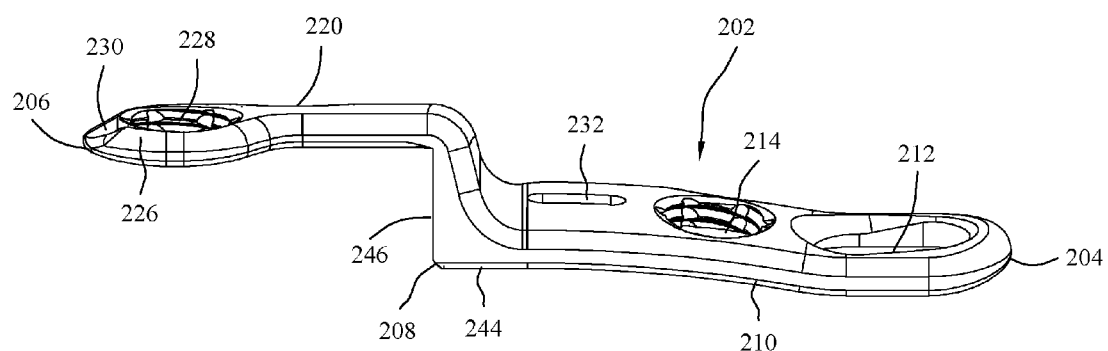
FIG. 12 is a second side view of the step off bone plate of FIG. 9, in accordance with an aspect of the present invention.
Figure 13:
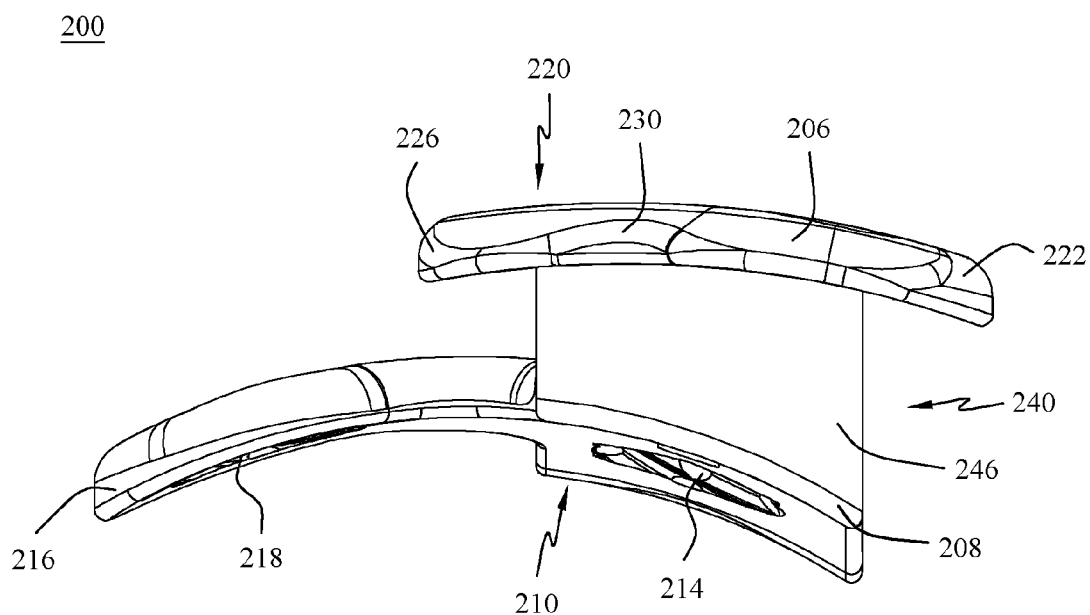
FIG. 13 is a front view of the step off bone plate of FIG. 9, in accordance with an aspect of the present invention.

As shown in FIGS. 9-16, the first portion 210 may have at least one slot 212 near the first end 204 of the body 202, at least one first opening 214 positioned adjacent the at least one slot 212, and at least one channel 232 positioned between the at least one first opening 214 and the transition point 208. As depicted, the at least one channel 232 may be positioned adjacent to the at least one slot 212. The slot 212, first opening 214, and channel 232 may be, for example, aligned along the center of the body 202. The slot 212 may be, for example, a compression screw hole for receiving a threaded fastener or screw (not shown). The opening 214 may be, for example, a screw hole for receiving a threaded fastener or screw (not shown). The channel 232 may be, for example, an opening for receiving an insertion tool. The first portion 210 may also include an extension member or arm 216, as shown in FIGS. 9-11 and 13-16. The extension member 216 may extend out from a side of the body 202 of the first portion 210 and may include at least one second opening 218. The extension member 216 may extend out from the body between the first end 204 and the transition point 208 and may be angled with respect to the longitudinal axis of the body 202. For example, the extension member 216 may extend out from the body near the first opening 214 and channel 232. The extension member 216 may be angled toward the second end 206 of the body 202. The extension member 216 may also be curved as it extends away from the body 202 as seen in FIG. 13. The curvature of the extension member 216 may, for example, match the curvature of the bone engaging the first portion 210. The extension member 216 may be configured to reinforce the plantar aspect of the foot to reduce or restrict gapping after surgery by providing plantar support from a medial positioned plate 200. The extension member 216 may also be positioned in the direction that matches the normal transition of forces during the gait cycle to provide the greatest strength during peak loads. The extension member 216 may be shorter than the extension member 116. In addition, the extension member 216 may be positioned closer to the transition point 208 than the extension member 116 is positioned to the transition point 108.

The first portion 210 of the plate 200 may include a dual curvature with, for example, a first curvature perpendicular to the long axis of the plate 200 and a second curvature along the long axis of the plate 200. The first curvature may have a radius of, for example, approximately 8 mm to 60 mm, and the second curvature may have a radius of, for example, approximately 50 mm to 300 mm. The first portion 210 near the first end 204 and including the slot 212 may be angled relative to the second curvature, as shown in FIGS. 11 and 12.

Figure 15:
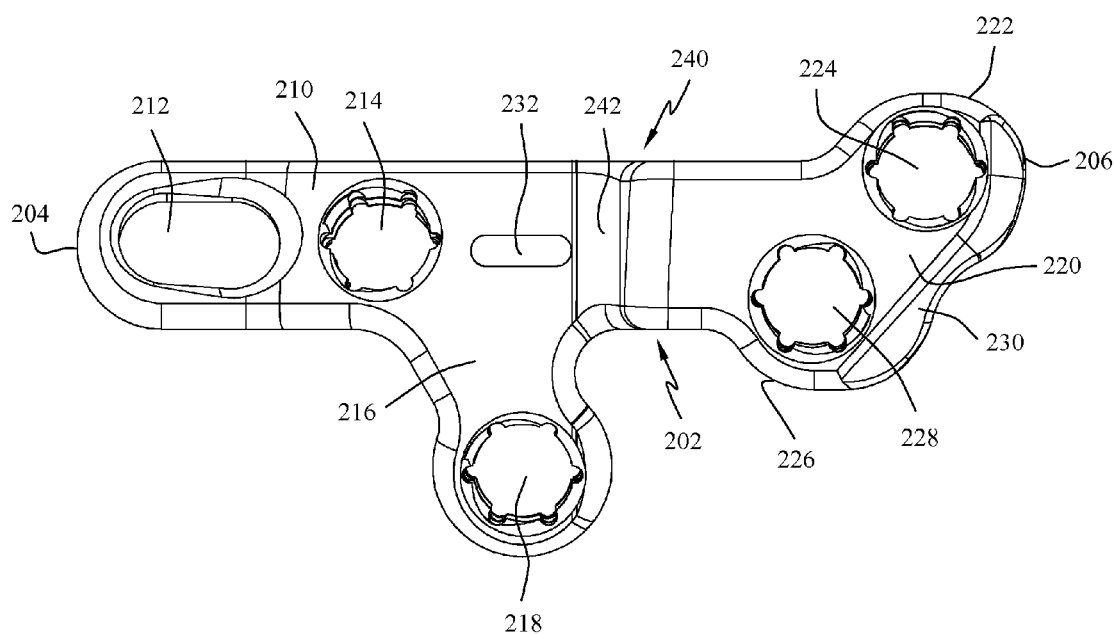
FIG. 15 is a top view of the step off bone plate of FIG. 9, in accordance with an aspect of the present invention.
Figure 16:
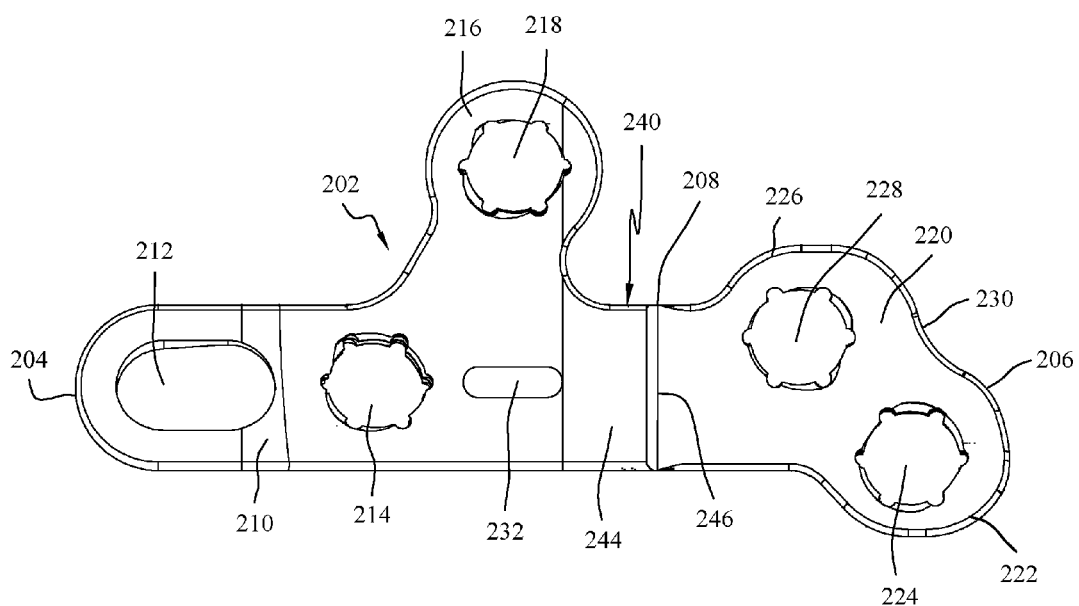
FIG. 16 is a bottom view of the step off bone plate of FIG. 9, in accordance with an aspect of the present invention.

The second portion 220, as shown in FIGS. 9-10 and 15-16, may include a first lobe 222 and a second lobe 226 extending out from the body 202. The first lobe 222 may be offset from the second lobe 226 forming an angled surface at the second end 206 of the body 202 as seen in FIG. 15. The first lobe 222 may include a third opening 224 and the second lobe 224 may include a fourth opening 228. Alternative numbers of lobes 222, 226 are also contemplated to provide for additional fastening locations for securing the plate 200 to the patient's bones. The openings 224, 228 may be, for example, screw holes for receiving threaded fasteners or screws (not shown). The second portion 220 may also include a ramped portion 230 positioned at the second end 206 along the angled surface. The ramped portion 230 is gradually angled from the bottom surface to the top surface of the body 202 and provides a surface that allows a tendon, for example, the anterior tibialis tendon, to glide over the plate 200. The ramped portion 230 has a more pronounced angle than the ramped portion 130. As discussed in greater detail above with respect to ramped portion 130, by allowing the tendon to glide over the plate soft-tissue irritation is eliminated. The ramped portion 230 may decrease the thickness of the plate at the second end 206, while still maintaining adequate thickness to prevent screw prominence.

Referring now to FIGS. 9-12, the connecting portion 240 is positioned relatively perpendicular to and couples the first portion 210 and the second portion 220. The connecting portion 240 provides a change in elevation or "step up" from the first portion 210 to the second portion 220. The connecting portion 240 may provide a step up of, for example, approximately 1 mm to 10 mm. The connecting portion 240 may include a sloped surface 242 on the top of the body 202. In addition, the connecting portion 240 may include a first transition portion 244 extending from the first portion 210 to the transition point 208 and a second transition portion 246 extending perpendicular to the first transition portion 244 from the transition point 208 to the second portion 220. The first transition portion 244 and second transition portion 246 may be relatively planar.

Figure 14:
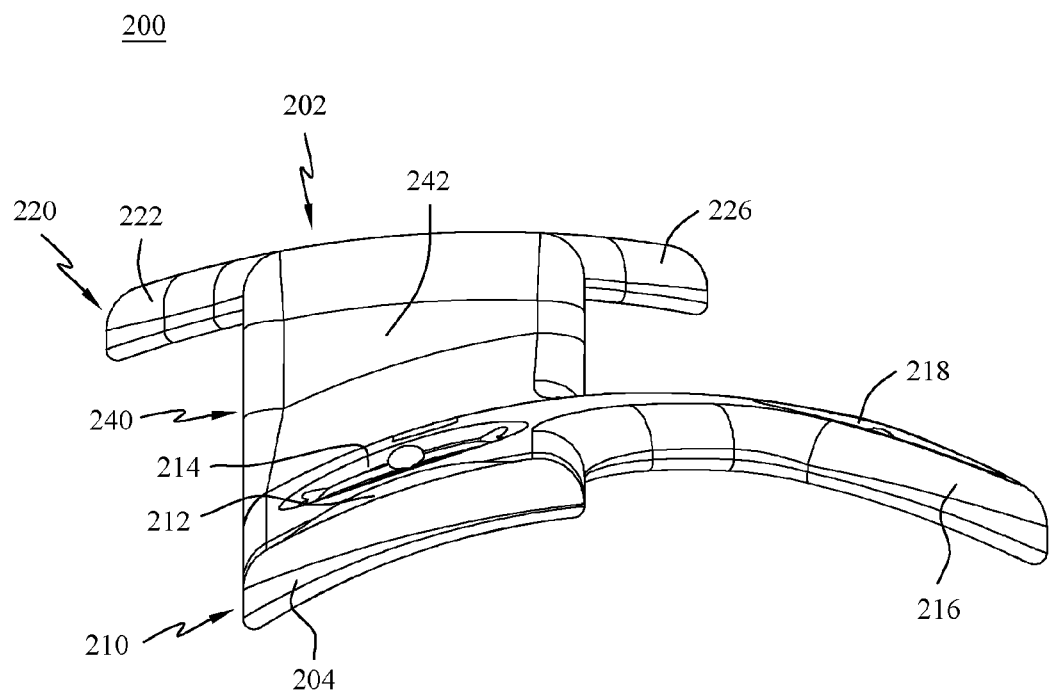
FIG. 14 is a back view of the step off bone plate of FIG. 9, in accordance with an aspect of the present invention.

As shown in FIGS. 11-16, the plate 200 may include multiple curved surfaces. The plate 200 may include dual curvatures with respect to the longitudinal axis of the plate 200, as shown in FIGS. 13-14. The first portion 210 may have a first curvature in a medial-lateral direction with respect to the longitudinal axis of the plate 200. The first curvature may have a range of, for example, approximately 8 mm to 60 mm. The second portion 220 may have a second curvature in the medial-lateral direction along with respect to the longitudinal axis of the plate 200 along the bottom surface. The second curvature may have a range from, for example, approximately 10 mm to 60 mm. The first curvature and second curvature may be different in plate 200 to allow for the plate 200 to be used on the medial aspect of a patient's foot. As shown in FIGS. 11-12, the body 202 of the plate 200 may have a third curvature along a portion of the plate 200 in line with the longitudinal axis and the third curvature may have a range of, for example, approximately 50 mm to 300 mm. The first end 204 of the plate 200 may not be curved along the longitudinal axis of the plate. The plate curvatures may have radii that are positioned off axis to provide strength to the plates 100, 200 and to enable placement of the plates 100, 200 on the medial aspect of the patient's bone.

Referring now to FIGS. 17-21, a bone plate alignment guide apparatus 300 is shown. The bone plate alignment guide apparatus 300 may include a body 310, a coupling member 330, a guide pin tissue protector 340. The apparatus 300 may also include a guide wire or pin (not shown) and a fastener (not shown). The coupling member 330 may include a knob 332 and a shaft 334. The shaft portion 334 may include an engagement portion 336 for coupling to a bone plate, for example, bone plate 100 or 200, and a groove 338 which may assist with coupling the engagement portion 336 to a bone plate. The engagement portion 336 may be, for example, threaded to engage corresponding threads in an opening in a bone plate, deformable to be removeably press fit into the opening in the bone plate, or another similar configuration that achieves a coupling of the guide apparatus 300 to a bone plate, such as, bone plate 100, 200, or the like. The guide wire (not shown) may be, for example, a pin, k-wire, olive wire, or the like. The fastener (not shown) may be, for example, a compression screw, lag screw, headless screw, or a solid screw, for crossing a joint or fracture.

Figure 17:
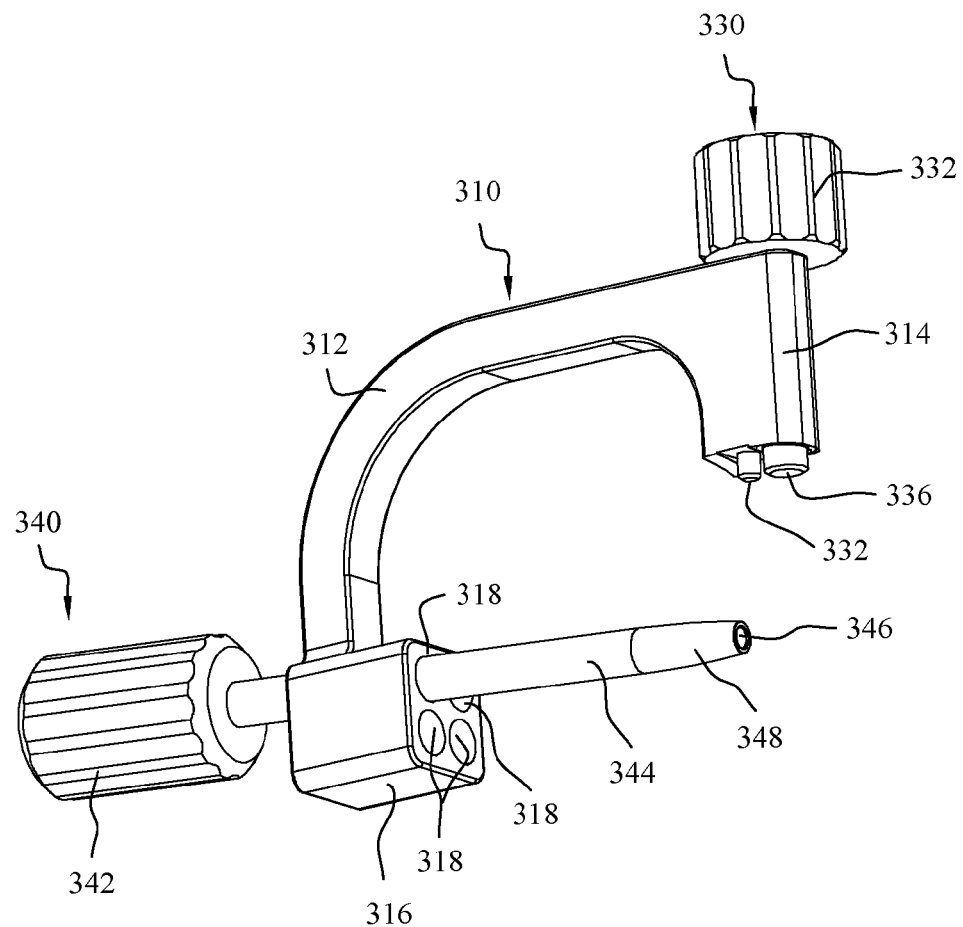
FIG. 17 is a perspective view of a bone plate alignment guide apparatus, in accordance with an aspect of the present invention.
Figure 18:
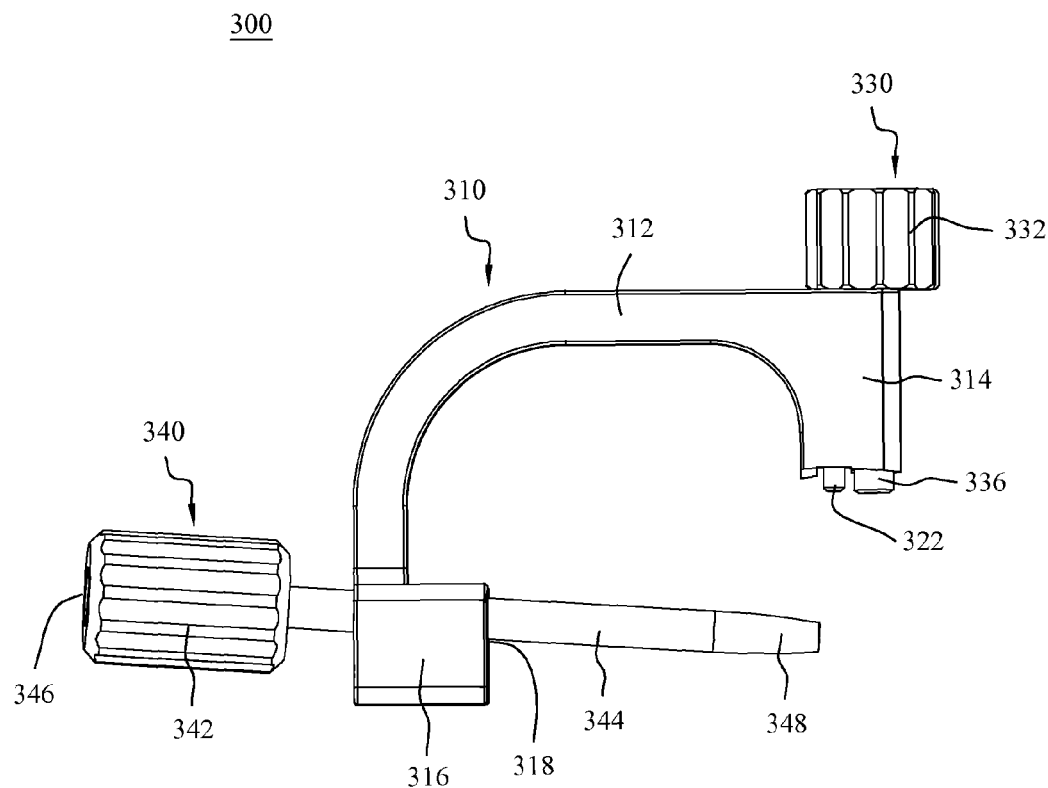
FIG. 18 is a side view of the bone plate alignment guide apparatus of FIG. 17, in accordance with an aspect of the present invention.
Figure 19:
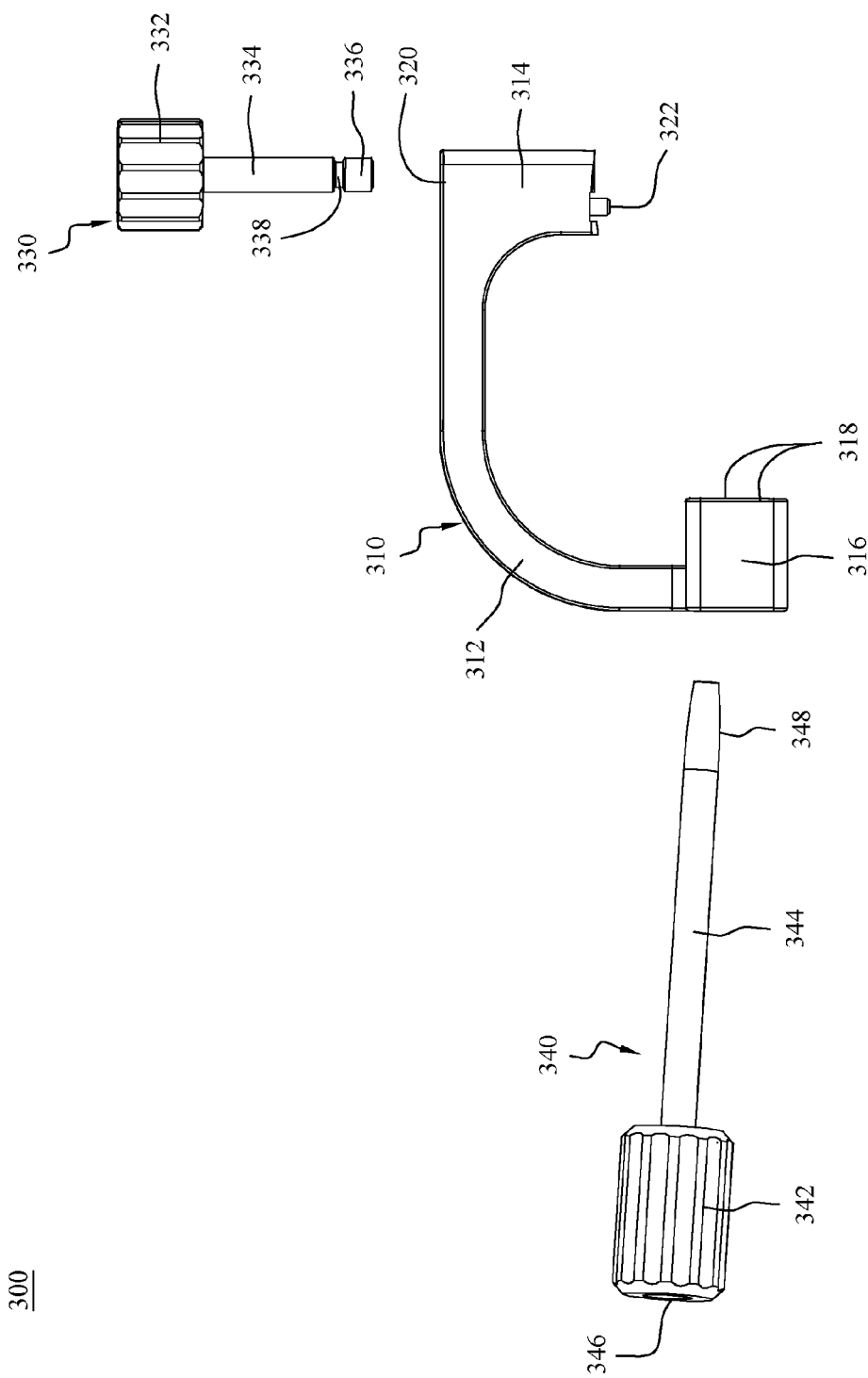
FIG. 19 is an exploded side view of the bone plate alignment guide apparatus of FIG. 17, in accordance with an aspect of the present invention.

The guide pin tissue protector 340, as shown in FIGS. 17-19, may include a handle portion 342 at a first end and a shaft portion 344 extending away from the handle portion 342 to a tip 348 at a second end. The shaft 344 may taper at the second end to form the tip 348. The guide pin tissue protector 340 may also include a through hole 346 extending from the first end to the second end to enable a guide wire (not shown) to pass through the tissue protector 340 and engage the patient's bone.

Figure 20:
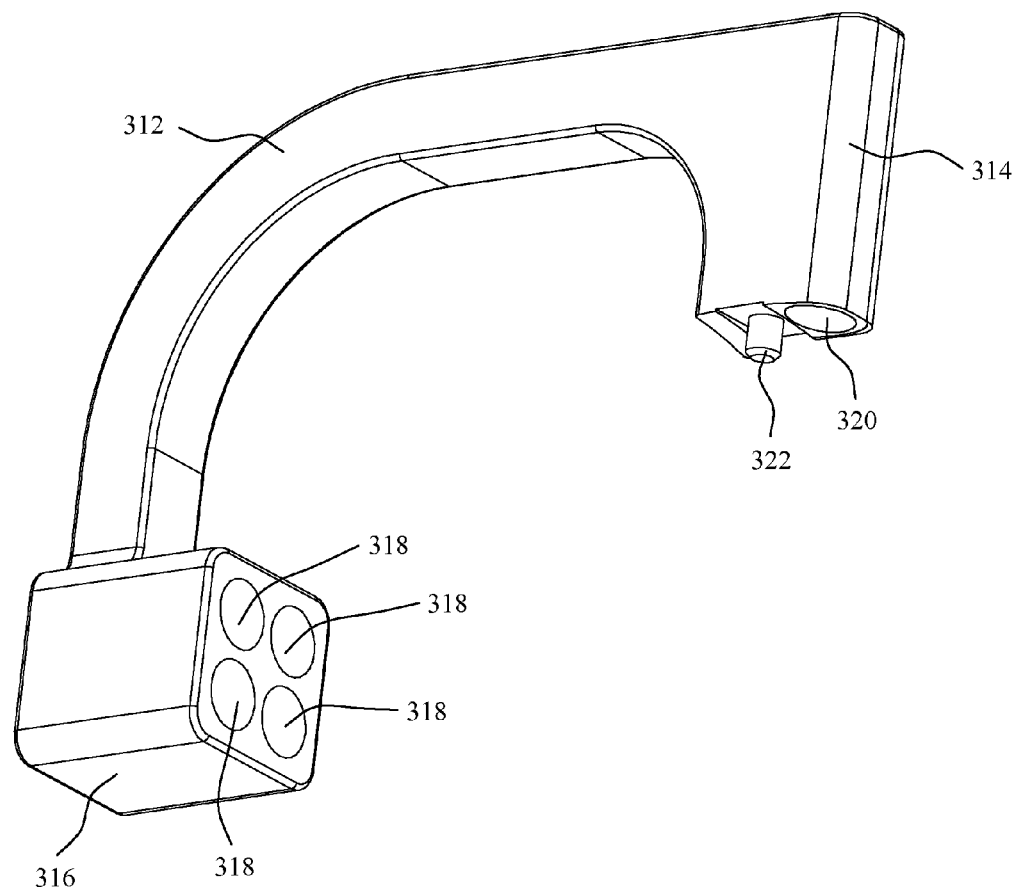
FIG. 20 is a bottom perspective view of the body of the bone plate alignment guide apparatus of FIG. 17, in accordance with an aspect of the present invention.
Figure 21:
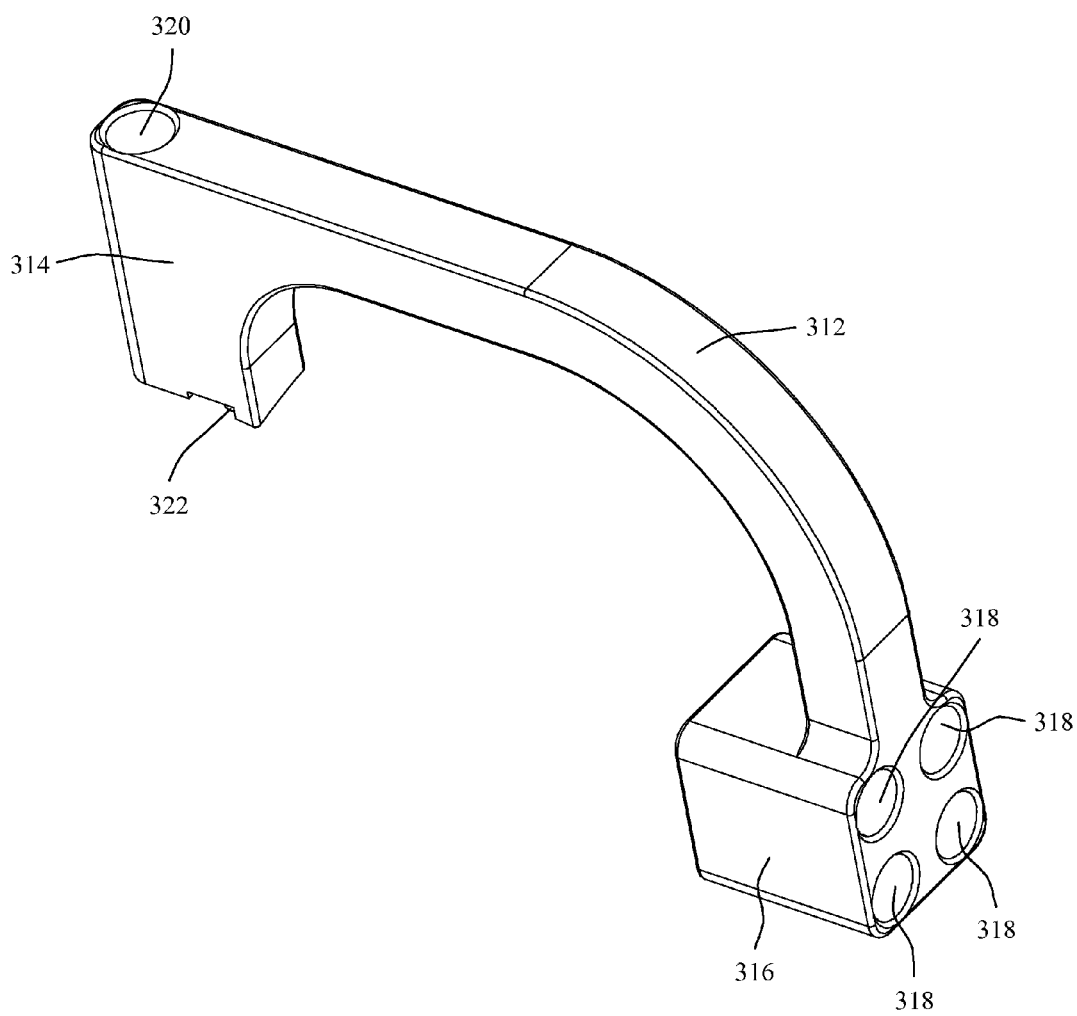
FIG. 21 is an end perspective view of the body of the bone plate alignment guide apparatus of FIG. 17, in accordance with an aspect of the present invention.

As shown in FIGS. 17-21, the body 310 may include an arm 312 with an attachment portion 314 at a first end and an alignment portion 316 at a second end. The alignment portion 316 of the body 310 may be, for example, a variable hole alignment portion, and may include a plurality of holes 318. The plurality of holes 318 may be, for example four holes that are positioned in a square arrangement. The plurality of holes 318 may be straight or angled to a desired insertion position relative to the arm 312 of the body 310. By way of specific example, the two left holes and two right holes may, for example, each be slightly angled toward the center of the alignment portion 316 such that each of the side holes converge toward each other. In addition, the top two holes and the bottom two holes may each be slightly angled toward the center of the alignment portion 316 such that each of the holes converge toward each other. Alternative angled arrangements for the holes 318 are also contemplated to enable a fastener to be inserted across two bones into a position that will not be in the path of the bone plate screws when they are inserted. The body 310 may also include a through hole 320 in the attachment portion 314 of the body 310, as seen in FIGS. 20-21. Further, the body 310 may include an alignment protrusion 322 extending away from the attachment portion 314, as shown in FIGS. 17-20, for engaging an opening in a bone plate, such as bone plate 100, 200, or the like. The alignment protrusion 322 may be used to position the bone plate alignment guide apparatus 300 with respect to a bone plate.

The alignment guide 300 may be used with plates 100 and 200. The alignment guide 300 and plate 100 or 200 form a bone plate insertion system that allows for the insertion of a crossing fastener and the bone plate screws without either contacting the other. Thus, the bone plate insertion systems provide a surgeon the ability to precisely place the crossing fastener and bone plate screws without the need for additional imaging or trial and error, thereby improving the surgical procedure.

Figure 22:
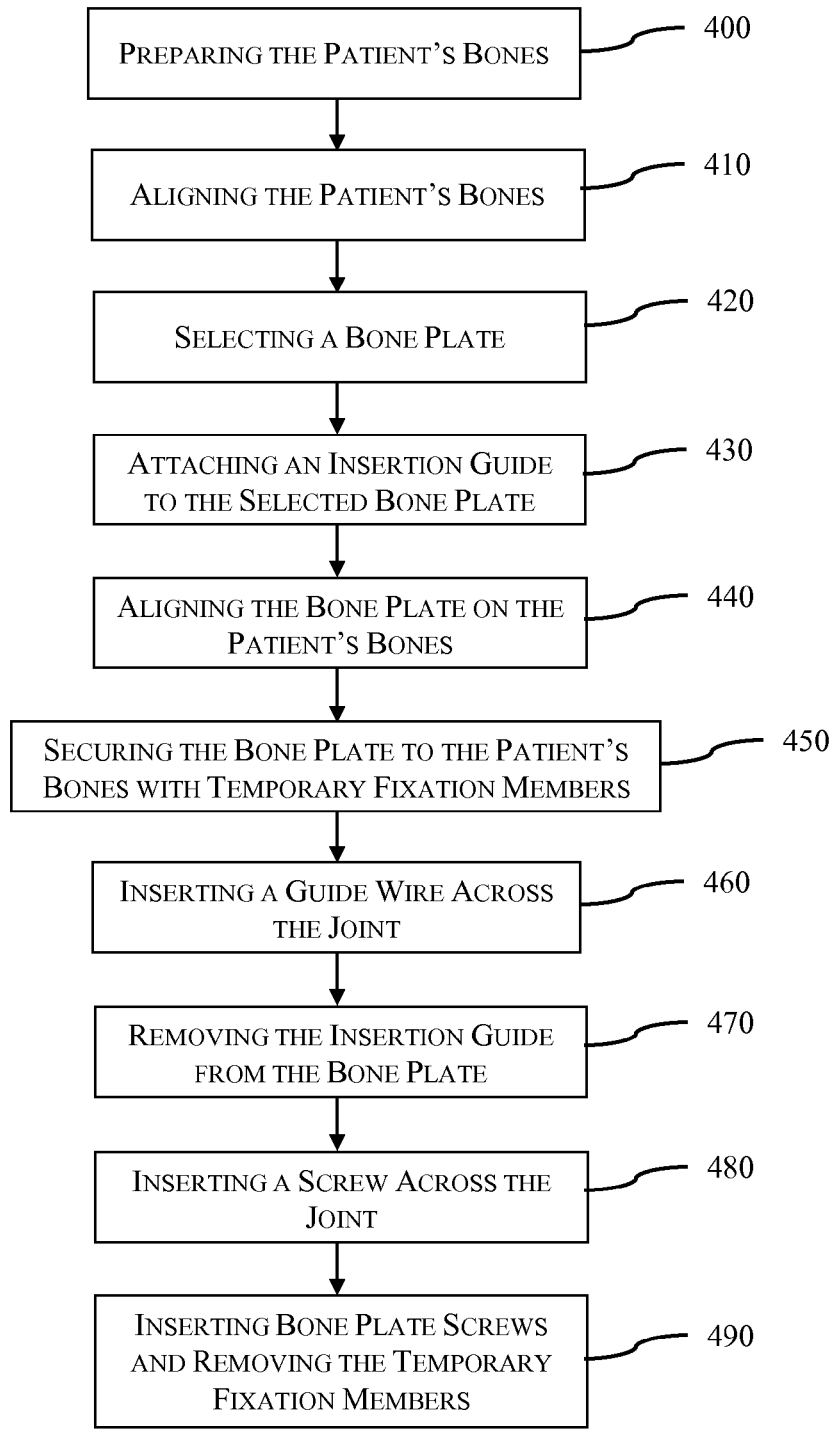
FIG. 22 depicts one embodiment of a method for using the step off bone plate, in accordance with an aspect of the present invention.

Referring now to FIG. 22, a method of using the step off bone plate systems 100, 200 is shown. As illustrated in FIG. 22, the method may include preparing the patient's bones 400 and aligning the patient's bones 410. Next, the method may include selecting a bone plate 420 and attaching an insertion guide to the bone plate 430. Once the bone plate is coupled to the insertion guide, the bone plate may be aligned on the patient's bones 440. Then, the bone plate may be secured to the patient's bones with temporary fixation members 450. After the bone plate is secured to the bones, a guide wire may be inserted across the patient's joint 460 and the insertion guide may then be removed from the bone plate 470. Next, the guide wire may be used to insert a screw across the joint 380. Finally, the screws may be inserted to secure the plate to the bones and the temporary fixation members removed 490.

The method as shown in FIG. 22 may be described in greater detail with reference to FIGS. 1-21. First, the surgeon will prepare the patient's bones by selecting the cartilage removal technique, for example, curettage or sagittal saw blade. If the surgeon selects to use a curettage, then the correction method will be translation of the bone, for example, the metatarsal. However, if the surgeon selects to use a sagittal saw blade, then the correction method will be angular correction of the joint, for example, the tarsometatarsal joint. Once the bones are prepared, they will be aligned for fixation and a guide wire may be inserted to temporarily stabilize the joint. The surgeon will then select a bone plate, for example, bone plate 100, 200 or another similarly shaped plate, which adequately spans the joint space. By way of specific example, the bone plates 100, 200 would likely be used when the surgeon is using a translation method to correct the deformity. Next, a bone plate alignment guide apparatus 300 may be secured to the selected bone plate 100, 200. The apparatus 300 may be secured by aligning the alignment protrusion 322 of the guide 300 with an opening (not shown) in the plate 100, 200 and inserting coupling member 330 through the opening 320 in the body 310 and securing the engagement portion 336 to another opening in the plate 100, 200.

Once the guide 300 is coupled to the plate 100, 200, the plate 100, 200 may be aligned onto the patient's bones. The plate 100, 200 is aligned with the long axis of the plate 100, 200 being parallel to the long axis of the bone, for example, metatarsal bone, to ensure proper orientation of the guide 300. Next, the plate 100, 200 is secured to the bones using at least two temporary fixation members, for example, olive wires. The first temporary fixation member may be inserted into the proximal screw hole in the plate 100, 200 and the second into a second opening in the plate 100, 200. For example, the first temporary fixation member may be inserted into openings 124, 128 or 224, 228 and the second temporary fixation member may be inserted into the slot 112, 212. After the plate 100, 200 is secured to the bones, the guide pin tissue protector 340 may be inserted into one of the through holes 318 in the body 310. Then, a guide wire may be inserted through the hole 346 and across the joint. Once the guide wire is determined to be in the correct position, the protector 340 may be removed from the body 310 and the coupling member 330 may be disengaged from the bone plate 100, 200 and the coupling member 330 and body 310 removed from the bone plate 100, 200.

After the guide 300 is removed, a screw insertion technique for inserting a crossing fastener, for example, a compression lag screw, may be employed to insert the crossing fastener through the joint. The crossing fastener is preferably inserted over the guide wire to obtain proper positioning to avoid contact with the bone plate screws when they are later inserted. Once the fastener is inserted, the guide wire may be removed. Next, screws (not shown) may be inserted into the patient's bones through the bone plate 100, 200. The screws may be inserted by, for example, using a threaded drill guide to drill the openings for the screws, then the openings are measured, and finally the screws are inserted into the openings. The screws may be, for example, locking screws, non-locking screws, or a combination thereof. The screws will be inserted without contacting the crossing fastener because the guide 300 correctly positions the crossing fastener such that it is not in the path of any of the bone plate screw openings. Once the plate 100, 200 is secured to the patient's bones, any olive wires, k-wires, or guide wires that have not yet been removed from the patient's bones may be removed. Finally, the patient's surgical opening may be closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A bone plate, comprising:
    a body with a first end and a second end, the body further comprising;
        a first portion with a first curvature;
        a second portion with a second curvature; and
        a connecting portion, wherein the connecting portion connects the first portion to the second portion and provides a change in elevation, wherein the connecting portion comprises:
            a sloped surface on a top of the body connecting a top surface of the first portion with a top surface of the second portion;
            a transition point positioned on a bottom of the body;
            a first transition portion on the bottom of the body and extending from the first portion to the transition point; and
            a second transition portion on the bottom of the body and extending perpendicular to the first transition portion from the transition point to the second portion;
        wherein the first curvature and the second curvature are curved in a transverse plane of the body, and wherein the first curvature is larger than the second curvature.

2. The bone plate of claim 1, wherein the first curvature ranges from 8 mm to 60 mm.

3. The bone plate of claim 1, wherein the body is curved along a longitudinal axis.

4. The bone plate of claim 3, wherein the curvature along the longitudinal axis ranges from 50 mm to 300 mm.

5. A bone plate, comprising:
    a body with a first end and a second end, the body further comprising;
        a first portion with a first curvature, wherein the first portion comprises:
            an extension arm extending away from a side of the body; and
            a slot extending through the first portion of the body near the first end;
        a second portion with a second curvature; and
        a connecting portion, wherein the connecting portion connects the first portion to the second portion and provides a change in elevation, wherein the connecting portion comprises:
            a sloped surface on a top of the body connecting a top surface of the first portion with a top surface of the second portion;
            a transition point positioned on a bottom of the body;
            a first transition portion on the bottom of the body and extending from the first portion to the transition point; and
            a second transition portion on the bottom of the body and extending perpendicular to the first transition portion from the transition point to the second portion.

6. The bone plate of claim 5, wherein the first portion further comprises:
    a first opening extending through the body adjacent to the slot; and
    a second opening extending through the extension arm.

7. The bone plate of claim 6, wherein the second portion comprises:
    a first lobe; and
    a second lobe offset from the first lobe.

8. The bone plate of claim 7, wherein the second portion further comprises:
    a ramped surface on the second end of the body, wherein the ramped surface decreases the thickness of the bone plate at the second end.

9. The bone plate of claim 8, wherein the ramped surface is angled from a bottom surface of the body to a top surface of the body.

10. The bone plate of claim 9, wherein the first lobe and second lobe each include an opening extending from a top surface of the second portion through a bottom surface of the second portion.

11. The bone plate of claim 10, wherein the connecting portion comprises a distance between the bottom surface of the first portion and the top surface of the second portion, wherein the distance is perpendicular to the longitudinal axis of the body.

12. The bone plate of claim 11, wherein the first portion is fixed to a bottom of the connecting portion and the second portion is fixed to a top of the connecting portion.

13. The bone plate of claim 12, wherein the first portion is offset in a vertical direction from the second portion.

14. The bone plate of claim 5, wherein the extension arm is curved along the first curvature of the first portion and angled toward the second portion.

15. A bone plate insertion system, comprising:
a bone plate with a first end and a second end, the bone plate further comprising;
   a first portion with a first curvature;
   a second portion with a second curvature; and
   a connecting portion, wherein the connecting portion connects the first portion to the second portion and provides a change in elevation between the first portion and the second portion, wherein the connecting portion comprises:
      a sloped surface on a top of the body connecting a top surface of the first portion with a top surface of the second portion;
      a transition point on the bottom of the body;
      a first transition portion on the bottom of the body and extending from the first portion to the transition point; and
      a second transition portion on the bottom of the body, extending perpendicular to the first transition portion from the transition point to the second portion; and
an alignment guide apparatus, wherein the alignment guide apparatus comprises:
   a body comprising:
      an arm with a first end and a second end;
      an attachment portion at the first end for engaging the bone plate; and
      an alignment portion at the second end with at least one opening for positioning a crossing fastener.

16. The bone plate insertion system of claim 15, wherein the alignment guide apparatus, further comprises:
   a coupling member with a knob and a shaft, wherein the shaft passes through the attachment portion;
   a protector member with a handle portion and a shaft portion, wherein the shaft portion passes through the alignment portion;
   wherein the coupling member attaches the alignment guide apparatus to the bone plate.

17. The bone plate insertion system of claim 16, wherein the alignment portion is square.

18. A method for using a step off bone plate, comprising:
preparing and aligning a patient's bones;
selecting a step off bone plate;
attaching an insertion guide to the step off bone plate;
aligning the step off bone plate over the bones;
securing the bone plate to the bones with temporary fixation members;
inserting a guide wire through the insertion guide and across the bones;
removing the insertion guide from the step off bone plate;
inserting a crossing fastener over the guide wire and across the bones; and
inserting bone screws through the plate to secure the plate to the patient's bones, and wherein the insertion guide positions the crossing fastener to avoid intersecting with the bone screws.

19. The method of claim 18, wherein the step off bone plate comprises:
a body with a first end and a second end, the body further comprising;
   a first portion with a first curvature;
   a second portion with a second curvature; and
   a connecting portion, wherein the connecting portion connects the first portion to the second portion, and provides a change in elevation, wherein the connecting portion comprises:
      a surface on a top of the body connecting a top surface of the first portion with a top surface of the second portion;
      a transition point positioned on a bottom of the body;
      a first transition portion on the bottom of the body that extends from the first portion to the transition point; and
      a second transition portion on the bottom of the body extending from the transition point to the second portion.

* * * * *